(12) United States Patent
Albers (10) Patent No.: US 9,101,453 B2
(45) Date of Patent: Aug. 11, 2015

(54) UROLOGICAL REPAIR APPARATUS AND METHOD

(76) Inventor: Greg Harold Albers, Dundas, MN (US)

( * ) Notice: Subject to any disclaimer, the term of this patent is extended or adjusted under 35 U.S.C. 154(b) by 209 days.

(21) Appl. No.: 12/817,953

(22) Filed: Jun. 17, 2010

(65) Prior Publication Data

US 2011/0313535 A1    Dec. 22, 2011

(51) Int. Cl.
*A61F 2/04* (2013.01)
*A61F 2/06* (2013.01)

(52) U.S. Cl.
CPC .............. *A61F 2/04* (2013.01); *A61F 2002/048* (2013.01)

(58) Field of Classification Search
CPC ..................................... A61F 2/04; A61F 2/06
USPC ............... 623/1.1, 1.11, 1.12, 1.15, 1.2, 1.22, 623/1.28–1.3, 1.33, 1.37, 23.64–23.7; 604/8
See application file for complete search history.

(56) References Cited

U.S. PATENT DOCUMENTS

| | | | | |
|---|---|---|---|---|
| 3,155,095 A | * | 11/1964 | Brown | 606/154 |
| 5,893,887 A | * | 4/1999 | Jayaraman | 623/1.15 |
| 7,056,325 B1 | * | 6/2006 | Makower et al. | 606/153 |
| 2001/0010013 A1 | * | 7/2001 | Cox et al. | 623/1.15 |
| 2003/0027751 A1 | * | 2/2003 | Kovesdi et al. | 514/12 |
| 2003/0176909 A1 | * | 9/2003 | Kusleika | 623/1.11 |
| 2005/0113933 A1 | * | 5/2005 | Carter et al. | 623/23.7 |
| 2005/0125072 A1 | * | 6/2005 | Kolb | 623/23.7 |
| 2005/0276841 A1 | * | 12/2005 | Davis et al. | 424/443 |
| 2007/0191768 A1 | * | 8/2007 | Kolb | 604/104 |

* cited by examiner

*Primary Examiner* — Yashita Sharma
(74) *Attorney, Agent, or Firm* — Billion & Armitage; Richard E. Billion (57) ABSTRACT

A urological repair device includes a stent having a diameter that fits within a portion of a urological structure. The stent also has a length to bridge a distance between a first end of the urological structure and a second end of the urological structure. The stent includes at least one tapered end. The tapered end enables placement of the stent within the urological structure. A method of repairing a urological structure includes placing a first end of a substantially tubular urological structure over a first end of a tubular stent, and placing a second end of a substantially tubular urological structure over a second end of a stent, and attaching the first end of the substantially tubular urological structure, the second end of a substantially tubular urological structure, and the tubular stent to form a fluid passageway.

17 Claims, 10 Drawing Sheets

UROLOGICAL REPAIR APPARATUS AND METHOD

TECHNICAL FIELD

Various embodiments described herein relate to a urological repair apparatus and method.

BACKGROUND

Several urological structures are tubular and may need to be repaired either to reverse a previous operation or as a result of a trauma injury such as an accident. One tubular structure that is increasingly more commonly repaired is the vas deferens. The repair of the vas deferens reverses a previous vasectomy where the vas deferens is cut. In some instances a portion of the vas deferens is removed in the performance of a vasectomy. If the vas deferens was previously cut close to the testes or close to the body, the repair of the vas deferens can be complicated. By the same token, if a substantial length of the vas deferens is removed, the repair can also be complicated. The testes rise and fall to maintain a temperature within the testes and if too long a length of the vas deferens is removed, the reattachment of the two ends can interfere with the ability of the body to lower the testicles. Of course there are many reasons for seeking a reversal of a vasectomy. Such reversals are on the rise in the United States. Currently there are as many as 500,000 vasectomies performed each year in the United States and there are as many as 40,000 reversals performed each year. The reversals are on the rise and currently can only be performed in hospitals by physicians specializing in urology. As a result, the cost of the reversals is relatively high.

One tubular structure that can be damaged as a result of a trauma is the ureter between the kidney and the bladder. For example, this particular ureter can be injured as a result of a car accident. The ureter needs to be repaired so that the patient can lead a more normal life after an operation. Problems arise when the ureter is damaged close to the kidney or close to the bladder. Of course other tubular structures may need to be reattached or repaired within a human. There also may be needs for such procedures in animals.

BRIEF DESCRIPTION OF THE DRAWINGS

The invention is pointed out with particularity in the appended claims. However, a more complete understanding of the present invention may be derived by referring to the detailed description when considered in connection with the figures, wherein like reference numbers refer to similar items throughout the figures and:

The description set out herein illustrates the various embodiments of the invention and such description is not intended to be construed as limiting in any manner.

DETAILED DESCRIPTION

Figure 1:
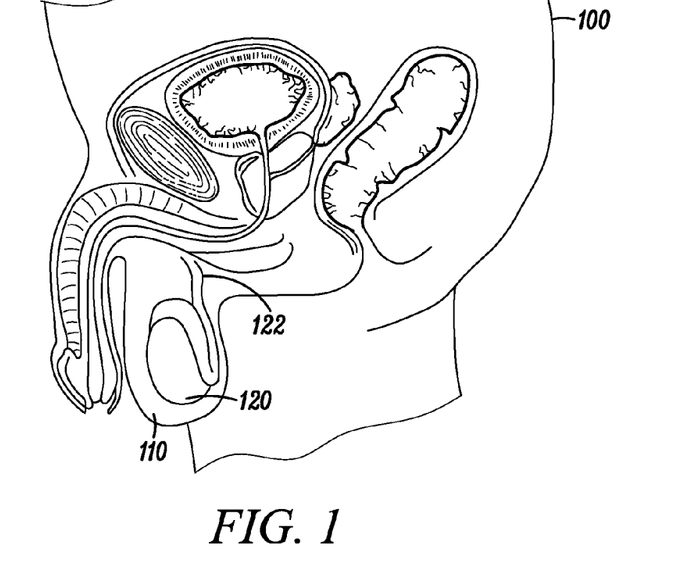
FIG. 1 is a view of a human body and includes the male reproductive organs.

FIG. 1 is a view of a human body 100 and includes the male reproductive organs 110. Specifically FIG. 1 is a side view of the body 100 that includes a testicle 112. The testicle is attached to the vas deferens 122. Common procedure of birth control for males includes a vasectomy. Vasectomy includes clipping the vas deferens and either tying off the two ends formed or cauterizing the two ends formed. The vas deforms 122 is the duct or tubular element that carries the sperm from the testicles to the reproductive area. By clipping the vas deferens 122 and tying off the two ends or cauterizing, the two ends, the male is unable to produce sperm to fertilize an egg of a female. As mentioned in the background, in many instances a male may decide to reverse a vasectomy.

Figure 2:
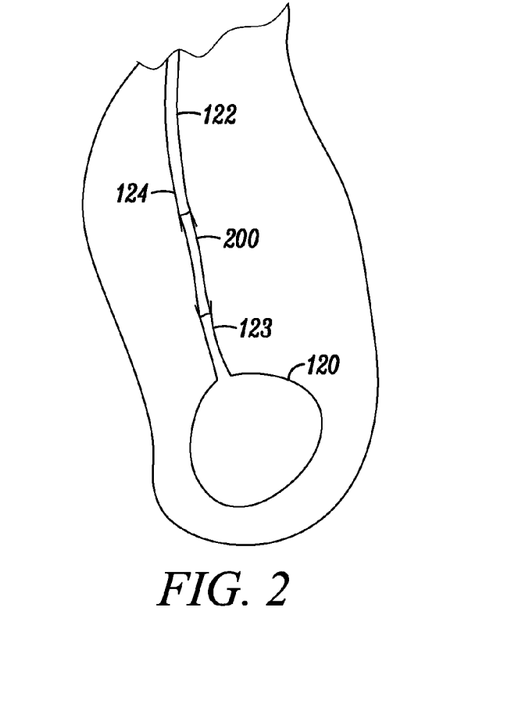
FIG. 2 is a schematic view of a testicle and vas deferens of the body, which includes a urological repair apparatus, according to an example embodiment.

FIG. 2 is a schematic view of a testicle 120 as housed in the body 100. As shown in FIG. 2 the vas deferens 122 has a first section 123 and a second section 124 which are joined by a urological repair apparatus 200, according to an example embodiment. The urological repair apparatus 200 includes a tubular portion having a diameter substantially equal to the diameter of the vas deferens 122. In some embodiments, the diameter is substantially constant while in other embodiments, the diameter is variable. The urological repair element or apparatus 200 has a first end which receives the end of one section 123 of the vas deferens 122 and has another end which receives the end of the vas deferens section 124. The urological repair apparatus 200 is hollow or is essentially tubular in structure. The urological repair apparatus 200 is made of a biocompatible material suitable for the application shown in FIG. 2. For example, the tubular apparatus may be made from a biocompatible material such as polyetheretherketone ("PEEK") or polytetrafluoroethylene (PTFE) which is known commercially as Teflon.

Figure 3:
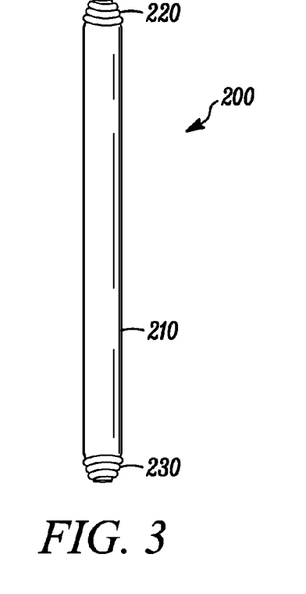
FIG. 3 is a top view of a urological repair apparatus, according to an example embodiment.
Figure 4:
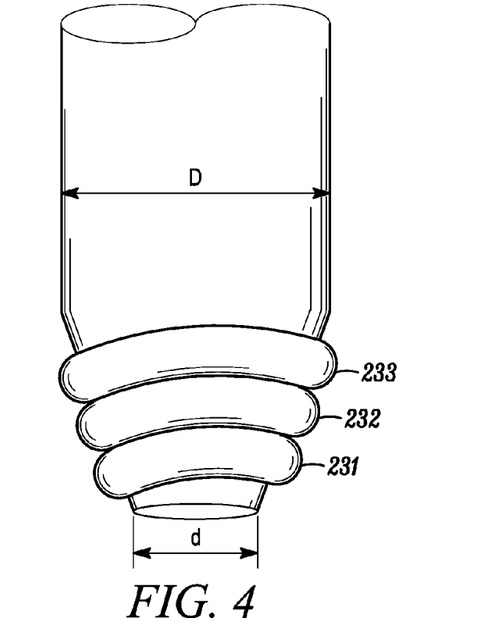
FIG. 4 is a top view of an end of a urological repair apparatus, according to an example embodiment.

FIG. 3 is a top view of the urological repair apparatus 200 according to an example embodiment. FIG. 4 is a top view of an end 230 of the urological repair apparatus 200, according to an example embodiment. Now referring to both FIGS. 3 and 4, the urological repair apparatus 200 will be further detailed. Urological apparatus 200 includes a main body 210, a first end 220, and a second end 230. Each of the ends 220, 230 are similar and therefore, for the sake of clarity, only one of the ends will be described. The main body 210 is a tubular structure. The tubular structure has an inside diameter "d" which may vary depending upon the application used for the urological repair apparatus 200. The ends 220, 230 may be tapered from the outside diameter toward the inside diameter of the tubular element. Also included on the tapered portions are a series of annular barbs such as 231, 232, 233. In the embodiment shown, the barbs 231, 232, 233 are not designed to pierce or otherwise penetrate the ends of the vas deferens. The barbs 231, 232, 233, have diameters that become successively larger. The barbs 231, 232, 233 are rounded and facilitate the attachment of tubular body elements, such as the vas deferens 122, to the end 230 of the urological repair apparatus 200. In other words the specific diameter "D" of the main body 210 of the urological repair apparatus 200 will generally be oversized with respect to the inner diameter of the natural tubular portion, such as the vas deferens. The urological repair apparatus 200 fits into the vas deferens.

The successively larger annual barbs 231, 232, 233 will stretch the natural structure but do not damage the natural structure. The amount of stretch will provide a friction type of fit between the natural structure, such as the vas deferens 122, and the end 230 of the urological repair apparatus 200. Although, as shown, the barbs present no sharp edges for damaging the natural structure, in some embodiments a sharp barb or different type of barb may be employed on the end 230 of the urological repair apparatus 200. It should be noted that as shown in FIG. 3, the end 220 and the end 230 of the urological repair apparatus 200 are substantially the same. As a result it is not necessary to also describe the end 220. However, in other embodiments, two different sizes of ends may be employed. In addition, the body need not have a constant diameter. In some embodiments, the diameter varies over the length of the urological repair apparatus 200.

Figure 5:
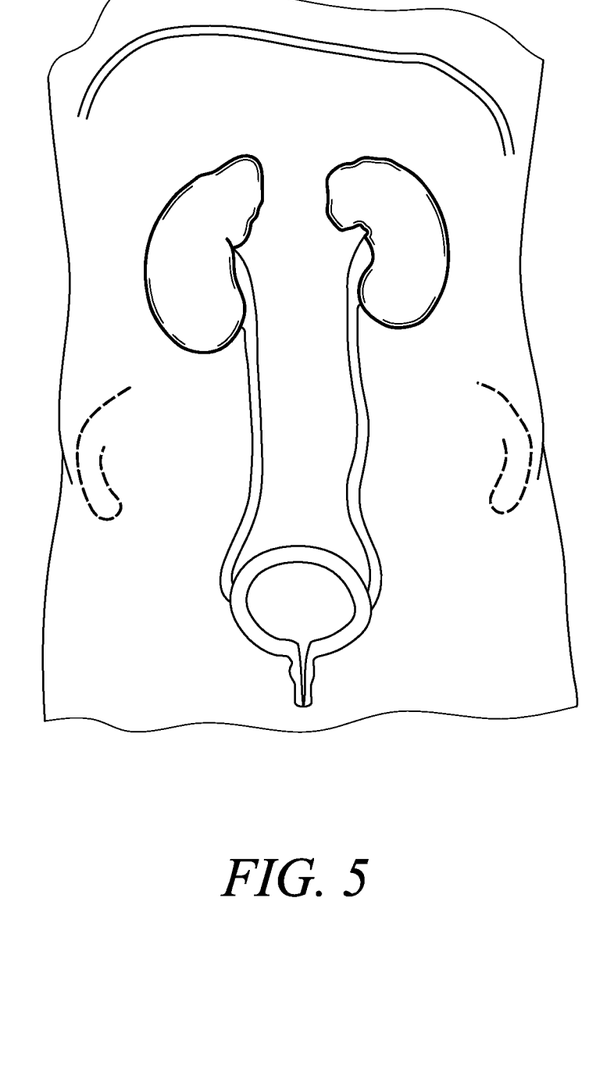
FIG. 5 is a front view of the human body that shows the right kidney, the left kidney, and a bladder.

FIG. 5 is a front view of the human body that shows the right kidney 180 the left kidney 182 and a bladder 184. Also shown in FIG. 5 are a ureter 190 which attaches the first kidney 180 to the bladder 184 and a second ureter 192 that connects the kidney 182 to the bladder 184. The ureters basically are natural tubular structures that drain the fluids from the kidney 180 and the kidney 182 into the bladder 184. As mentioned above, the ureters 190, 192 may be damaged and may be in need of repair.

Figure 6:
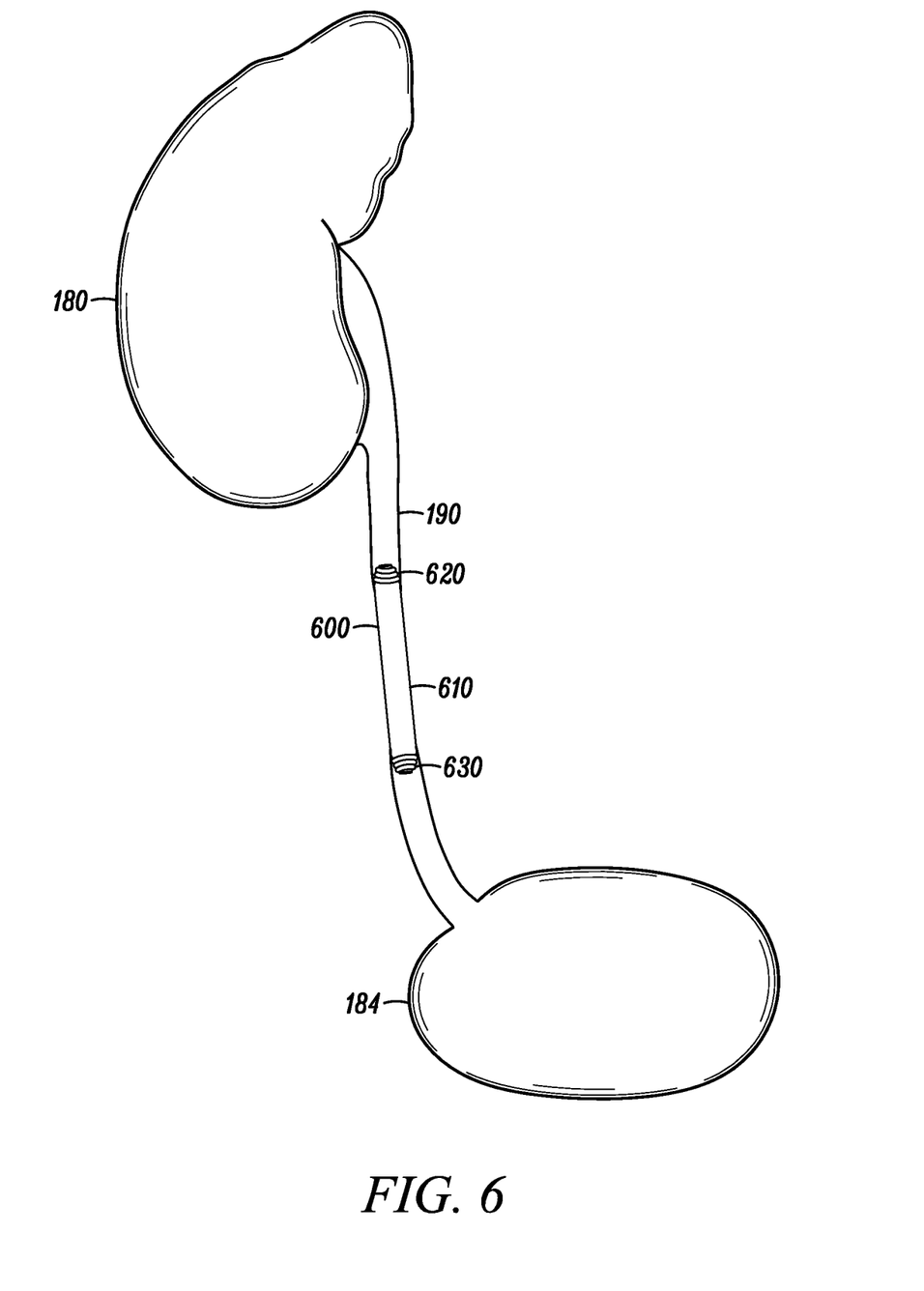
FIG. 6 is a schematic view of a ureter that includes an embodiment of the urological repair apparatus, according to an example embodiment.

FIG. 6 is a schematic diagram of kidney 180 and the bladder 184 which includes a ureter 190 that has been repaired using a urological repair apparatus 600. It should be noted that the urological repair apparatus 600 is substantially the same as the urological repair apparatus 200. However the size of the structure will be different for the different application. In other words, the ureter repair apparatus 600 will be longer than the urological repair apparatus 200 in many applications. The ureter repair apparatus may also have other dimensions that differ from the dimensions associated with the urological repair apparatus 200. However the elements of the urological repair apparatus 600 will be substantially the same as the urological repair apparatus 200. One of the differences is that the end features, such as on ends 220 and 230 will be scaled up to form an end 620 and an end 630. In addition the diameter or inner diameter "d" and the outer diameter "D" (not shown in FIG. 6) will also be scaled up in the larger sized urological repair apparatus 600. The ureter 190 is generally a larger natural tubular structure than the vas deferens. The ends 620, 630 of the urological repair apparatus 600 will also include a barbed structure such as that described with respect to FIGS. 3 and 4. The urological repair apparatus 600 will be made of a biocompatible material. However, the urological repair apparatus 600 must be able to transport acidic material or acidic fluids in the application where it is placed into the ureter. As a result, the material of the urological repair apparatus must be both biocompatible with the human body as well as able to transport an acidic fluid without deteriorating prematurely. The material must also be approved by the United States Food and Drug Administration (FDA). Biocompatible materials such as PEEK and Teflon are two biocompatible materials that meet these criteria.

It should also be noted that for each application, such as the urological repair apparatus 200 for the repair of the vas deferens, and for the urological repair apparatus 600 for repair of the ureter, it may be necessary to have different lengths for the main bodies of these two respective devices. The different lengths accommodate different sized human beings as well as different lengths of natural material that must be replaced. The amount of natural material that may have been removed in a surgical procedure depends on the damage suffered in an accident. In other words, the main body 210 of the urological repair apparatus 200 may come in several lengths. Similarly the main body 610 of the urological repair apparatus 600 may also come in several lengths.

Figure 7:
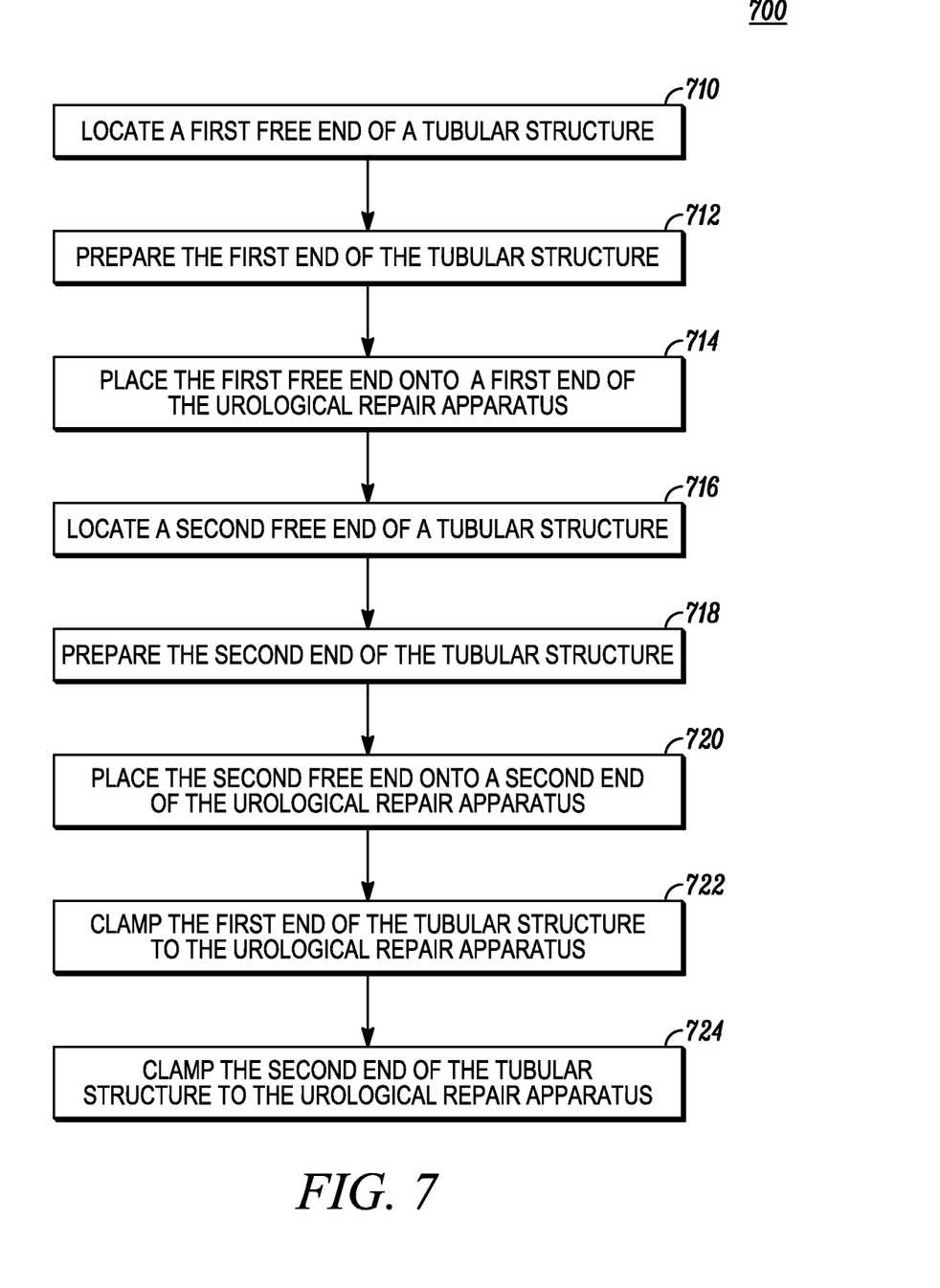
FIG. 7 is a flow chart of a method for using a urological repair apparatus, according to an example embodiment.

FIG. 7 is a flow chart of a method 700 for using a urological repair apparatus, according to an example embodiment. The method includes locating a first free end of a tubular structure 710, and preparing the first end of the tubular structure 712. Preparing the end of the tubular structure 712 may include removing a portion of the tubular structure. For example, when a ureter is damaged or severed, a portion of the free end may have to be removed so that the free end is smooth and essentially free of defects. When reversing a vasectomy, preparing the end of the tubular structure 712 may include removing a previously cauterized end or previously knotted end of the vas deferens. The method 700 also includes placing the first free end onto a first end of the urological repair apparatus 714. The method 700 also includes locating a second free end of a tubular structure 716, preparing the second end of the tubular structure 718, and placing the second free end onto a second end of the urological repair apparatus 720. In some embodiments, the first end of the tubular structure may have to be clamped to the urological repair apparatus 722 and the second end of the tubular structure may have to be clamped to the urological repair apparatus 724.

Figure 8:
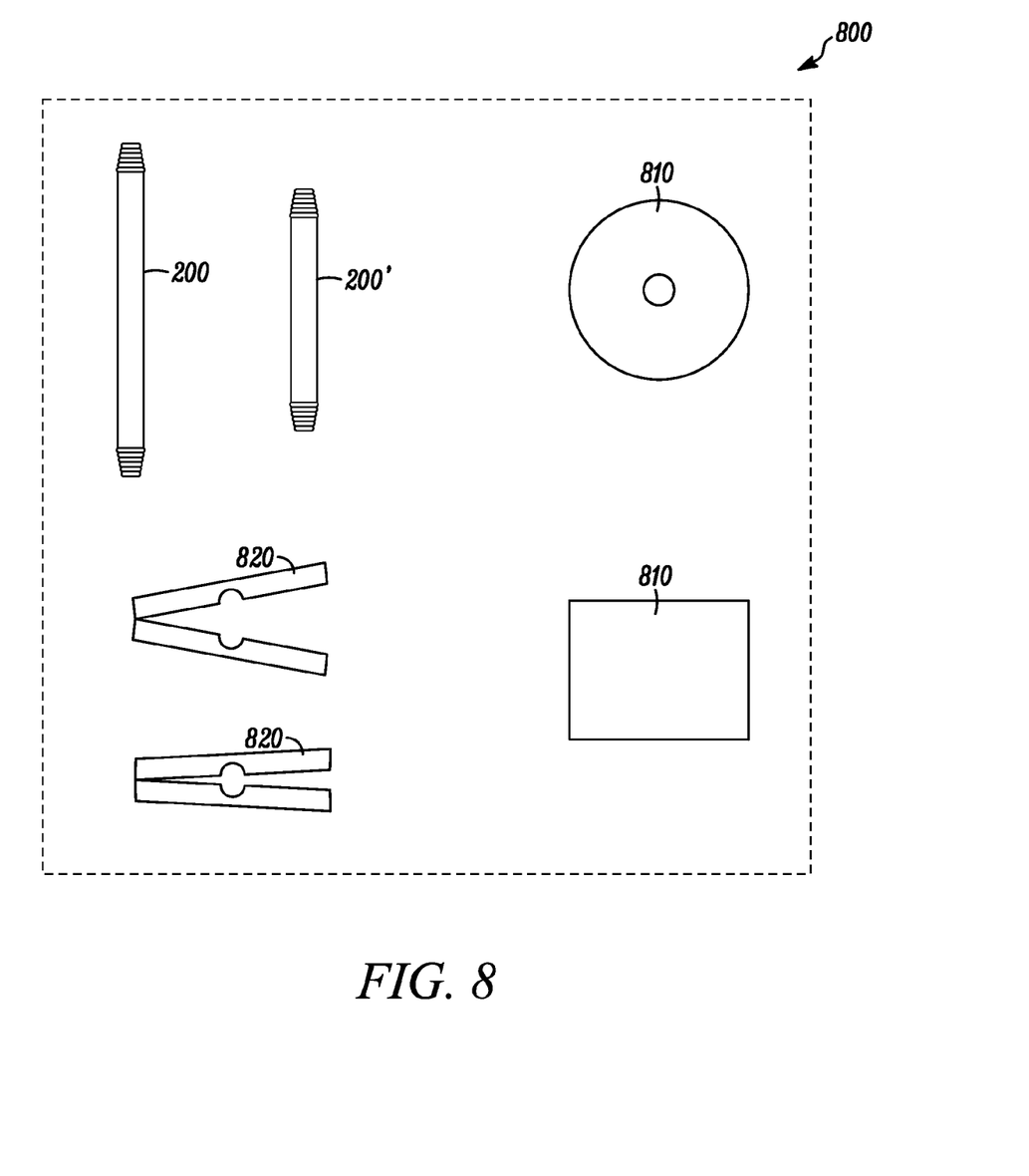
FIG. 8 is a view of a kit that includes at least one urological repair apparatus and a set of instructions for using the urological repair apparatus, according to an example embodiment.

FIG. 8 is a view of the kit 800 that includes at least one urological repair apparatus 200, 600 and a set of instruction for using the urological repair apparatus 200, 600 according to an example embodiment. The kit 800 will typically be put together for a particular urological repair. Therefore for the sake of simplicity, a kit 800 for that includes a urological repair apparatus 200 for reversing a vasectomy will be discussed by way of an example. It should be noted that similar kit may be put together for repairing ureters. The kit 800 can include a number of urological repair apparatuses 200, 200. Typically the kit 800 will include at least one urological repair apparatus 200 having a desired length. In some kits, however, a plurality of urological repair apparatuses 200, 200 of varying lengths can be included so that as a repair is being made, one of several lengths of urological repair apparatuses 200, 200 can be selected. Also included in the kit is a set of instructions 810. The instructions can include written instructions about the procedure and how to use the urological repair kit. The instructions 810 in some embodiments may include a compact disc or DVD that will show actual motion pictures or still pictures of the procedure. In addition, the kit 800 can include a set of biocompatible clamps 820. The biocompatible clamps 820 will include an opening therein so that the natural tubular structure that is being repaired can be clamped to the urological repair apparatus 200. It is contemplated that in many instances a clamp from the set of clamps 820 may not be needed since the barbed ends of the urological repair apparatus will hold the natural tubular structure in place with respect to the end of the urological repair apparatus. However, a set of clamps 820 is included as further assurance to prevent slippage or a disconnect between the tubular repair apparatus 200 and of the natural structure such as the vas deferens, that is being attached to the tubular repair apparatus. It should be noted that the clamps are made of a biocompatible material and that there may be more clamps included than are actually needed to perform the urological repair in the event that one clamp should be lost or dropped or the like.

Figure 9:
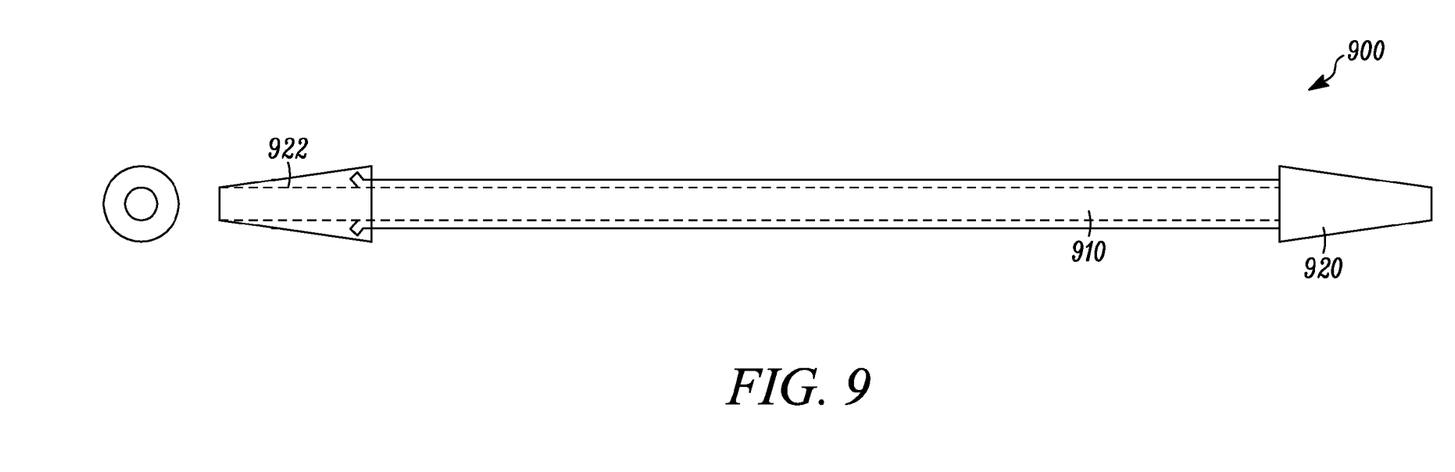
FIG. 9 is a perspective view of another urological repair apparatus, according to another example embodiment.

FIG. 9 is a perspective view of another urological repair apparatus, according to another example embodiment. The urological repair apparatus 900 includes a tubular body 910 having an inside diameter of approximately 0.022". The tubular body includes a wall having a wall thickness of 0.005". The outer diameter of the tubular body 910 is 0.032". The tubular body includes a first overmolded tip 920 and a second overmolded tip 922. The overmolded tips 920, 922 are located at the ends of the tubular body 910. The overmolded tip is approximately 0.1000" long and has an outside diameter of 0.050" which tapers down to the inside diameter of 0.022" over the 0.1000" length of the body tip 920, 922. The flare dimension is less than 45 degrees over the length of the tip 920, 922. In some embodiments, the angle is can be as small as 15 degrees. Generally, the flare dimension is in the range of 10-45 degrees. The tips 920, 922 are placed within the urological structure. The overmolded tips 920, 922 hold the ends of the urological structure (such as the vans deferens) in place. The overall length can be any length. As shown, the length of the body 910 of the tubular structure is about 0.800".

Figure 10:
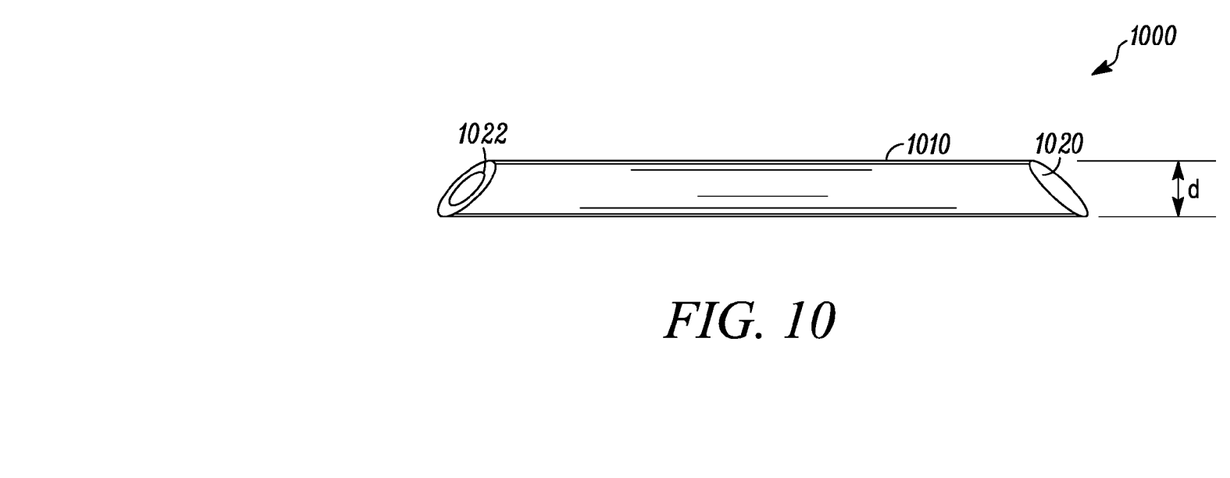
FIG. 10 is a perspective view of yet another urological repair apparatus, according to another example embodiment.

FIG. 10 is a perspective view of another urological repair apparatus 1000, according to yet another example embodiment. The urological repair apparatus 1000 has an outside diameter that allows it to fit within a urological structure. The urological structure can be a vas deferens in one instance. The outer diameter, 1010 would be in the range of 0.0300" to about 0.0500". This relatively small outer diameter would fit within the vas deferens. A urological repair apparatus 1000 having a larger inner diameter would be used to repair the ureter. The urological apparatus 1000 also includes a first beveled end 1020 and a second beveled end 1022. The beveled ends 1020, 1022 include an angle that allows the urological structure to be easily placed thereon. The angle is set so that the beveled end 1020, 1022 will not pierce the urological structure and yet will still ease the threading of the urological structure over the beveled end 1020, 1022. One cut end of the urological structure is placed over one beveled end 1020, and another cut end of the urological structure is placed over the other beveled end 1022. The cut ends of the urological structure can then be sewn together. The urological repair apparatus 1000 serves as a backstop in the event the surgeon sews the two ends of the urological structure (such as the vas deferens or ureter) together. It should be noted that in some embodiments, the surgeon can sew the ends and in some embodiments, a surgeon can place the ends over the tips of the urological repair apparatus 1000. In still other embodiments, the surface of the urological repair apparatus 1000 near the beveled ends 1020, 1022 is provided with a roughened or friction surface to enable the urological structure, such as the vas deferens, to stay in place if the urological repair apparatus is placed into the urological structure. The urological repair apparatus 1000 is formed of a biocompatible material. In one embodiment, the biocompatible material also breaks down in the body over time. In some embodiments, the urological repair apparatus may be coated or impregnated with a protein drip that promotes tissue growth.

Figure 11:
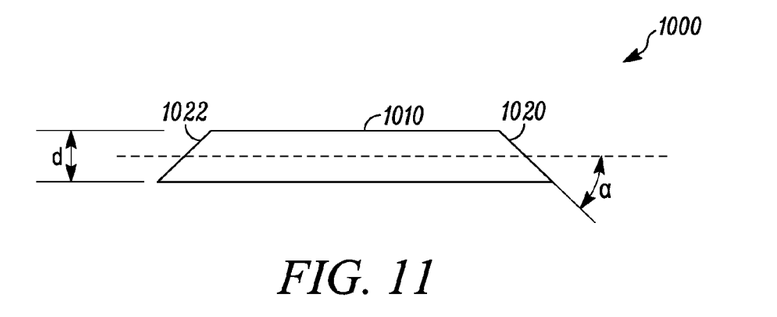
FIG. 11 is a perspective view of still another urological repair apparatus, according to another example embodiment.

FIG. 11 is a perspective view of still another urological repair apparatus 1100, according to another example embodiment. The urological repair apparatus 1100 has an outside diameter that allows it to fit within a urological structure. The urological structure can be a vas deferens in one instance. The outer diameter, 1110 would be in the range of 0.0300" to about 0.0500". This relatively small outer diameter would fit within the vas deferens. A urological repair apparatus 1100 having a larger inner diameter would be used to repair the ureter. The urological apparatus 1000 also includes a first beveled end 1120 and a second beveled end 1122. The beveled ends 1020, 1022 include an angle that allows the urological structure to be easily placed thereon. The angle is set so that the beveled end 1120, 1122 will not pierce the urological structure and yet will still ease the threading of the urological structure over the beveled end 1120, 1122. The main difference between the urological repair apparatus 1100 and the urological repair apparatus 1000 is that the former has a shorter length. One cut end of the urological structure is placed over one beveled end 1120, and another cut end of the urological structure is placed over the other beveled end 1122. The cut ends of the urological structure can then be sewn together. The urological repair apparatus 1100 serves as a backstop as the surgeon sews the two ends of the urological structure (such as the vas deferens or ureter) together. The urological repair apparatus 1100 is formed of a biocompatible material. In one embodiment, the biocompatible material also breaks down in the body over time. In some embodiments, the urological repair apparatus may be coated or impregnated with a protein drip that promotes tissue growth.

Figure 12:
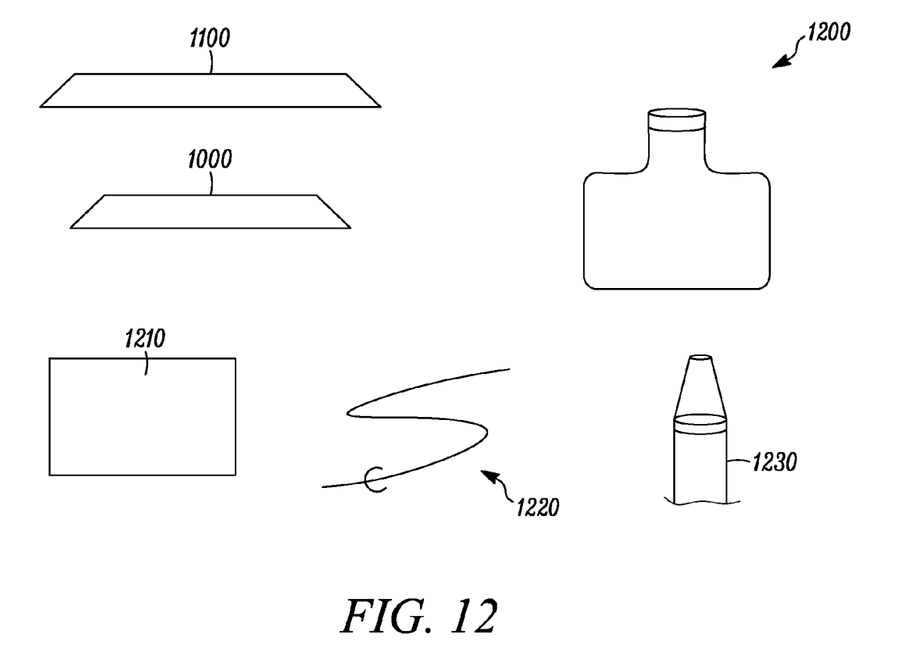
FIG. 12 is a view of another kit that includes at least one urological repair apparatus and a set of instructions for using the urological repair apparatus, according to an example embodiment.

FIG. 12 is a view of another kit 1200 that includes at least one urological repair apparatus and a set of instructions for using the urological repair apparatus, according to an example embodiment. The kit 1200 will typically include the necessary elements needed for a particular urological repair. Therefore for the sake of simplicity, a kit 1200 for that includes a urological repair apparatus 1100 for reversing a vasectomy will be discussed by way of an example. It should be noted that similar kit may be put together for repairing ureters. The kit 1200 can include a number of urological repair apparatuses 1100, 1000, 900, 200. Typically the kit 1200 will include at least one urological repair apparatus 1100 having a desired length. In some kits, however, a plurality of urological repair apparatuses 1000, 1100 of varying lengths can be included so that as a repair is being made, one of several lengths of urological repair apparatuses 1000, 1100 can be selected. Also included in the kit is a set of instructions 1210. The instructions can include written instructions about the procedure and how to use the urological repair kit. The instructions 1210 in some embodiments may include a compact disc or DVD that will show actual motion pictures or still pictures of the procedure. In addition, the kit 1200 can include a suture setup 1220 for sewing the ends of the urological structure, such as the vas deferens together. The kit 1200 can also include a protein that can be placed on the selected urological repair apparatus. It is contemplated that the kit can also include a vial of protein drip 1230. It is further contemplated, that the protein drip 1230 may not be needed since the urological repair apparatus is made of a biocompatible material and the ends of the urological structure will heal together without the protein drip 1230. It should be noted that there may be more materials in a kit than are actually needed to perform the urological repair. This provides the surgeon with options some of which may merely be a personal preference in performing a procedure.

A urological repair device includes a stent having a diameter that fits within a portion of a urological structure. In some embodiments, the stent also has a length to bridge a distance between a first end of the urological structure and a second end of the urological structure. The stent includes at least one tapered end. The tapered end enables placement of the stent within the urological structure. In one embodiment, the stent includes a first tapered end and a second tapered end. In one embodiment, the stent has an outside diameter sized to fit within a portion of a human ureter. In another embodiment, the stent has an outside diameter sized to fit within a portion of a human vas deferens. In another embodiment, the first tapered end and the second tapered end include a barb to hold a first portion of a ureter to the first tapered end of the stent and a second portion of the ureter to the second tapered end of the stent. In still another embodiment, the tapered end includes at least one bevel. A tapered end enables placement of the stent within the urological structure. The bevels may have specific angles. For example, the stent includes a first beveled end, and a second beveled end, and the angle of the bevel with respect to a centerline of the stent enables the placement of at least a portion of the stent into the vas deferens. The stent is made of a biocompatible material. In some embodiments, the stent is made of a bioresorbable material. The urological repair device can also include a liquid protein material for adding to the surface of the stent. The urological repair device also can include a length of suture material, and a sterile needle.

Figure 13:
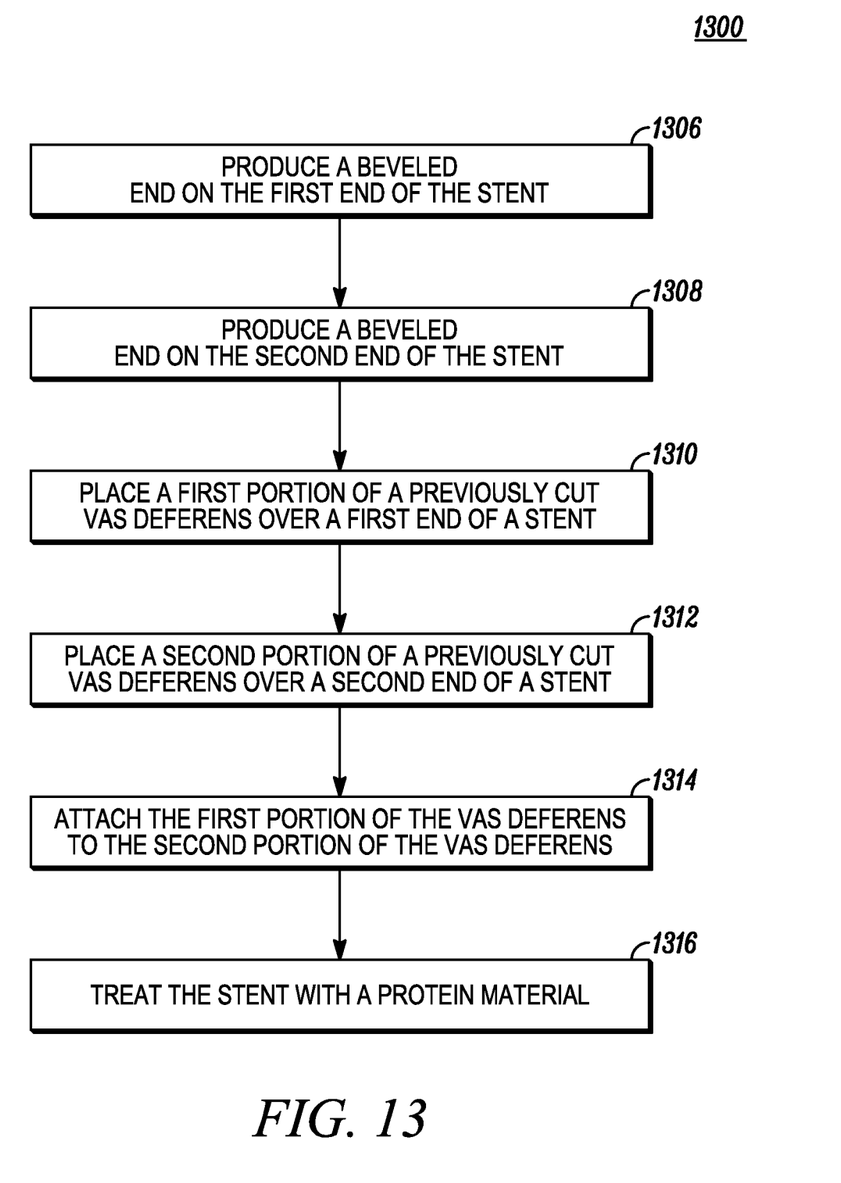
FIG. 13 is a flow chart of another method for using a urological repair apparatus, according to an example embodiment.

FIG. 13 is a flow chart of another method 1300 for using a urological repair apparatus, according to an example embodiment. The method 1300 for reattaching two portions of the vas deferens includes placing a first portion of a previously cut vas deferens over a first end of a stent 1310, placing a second portion of a previously cut vas deferens over a second end of a stent 1312, and attaching the first portion of the vas deferens to the second portion of the vas deferens 1314. The stent is sized to fit within the vas deferens. In one embodiment, attaching the first portion of the vas deferens to the second portion of the vas deferens 1314 includes sewing the first portion of the vas deferens to the second portion of the vas deferens. The two portions of the vas deferens are brought together over the stent. The stent serves as a backing material while the two portions of the vas deferens are stitched together. Scar tissue, if it should form, will form on the outside of the repaired vas deferens. Without the stent, there is a possibility that scar tissue can grow toward the inner portion of the vas deferens resulting in scar tissue partially blocking or totally blocking fluid flow through the vas deferens. In another embodiment, the two portions of the vas deferens are attached 1314 by adhering the first portion of the vas deferens to the second portion of the vas deferens. The method may also include treating the stent with a protein material 1316. The protein material enhances the growth of the vas deferens. In one embodiment, the protein material is a liquid protein solution. The surface of the stent, and more particularly, the outside surface of the stent, are treated with the liquid protein solution. The method for reattaching two portions of the vas deferens of can also include producing a beveled end on the first end of the stent 1306, and producing a beveled end on the second end of the stent 1308. Producing a beveled end on the first end of the stent 1306 includes forming a bevel having an angle with respect to the length of the stent that eases placement of the first end of the stent into the first portion of the vas deferens. Similarly, producing a beveled end on the second end of the stent 1308 includes forming a bevel having an angle with respect to the length of the stent that eases placement of the second end of the stent into the second portion of the vas deferens. In some embodiments, the stent used in the method is made of a bioresorbable material that reabsorbs into the body over time.

Figure 14:
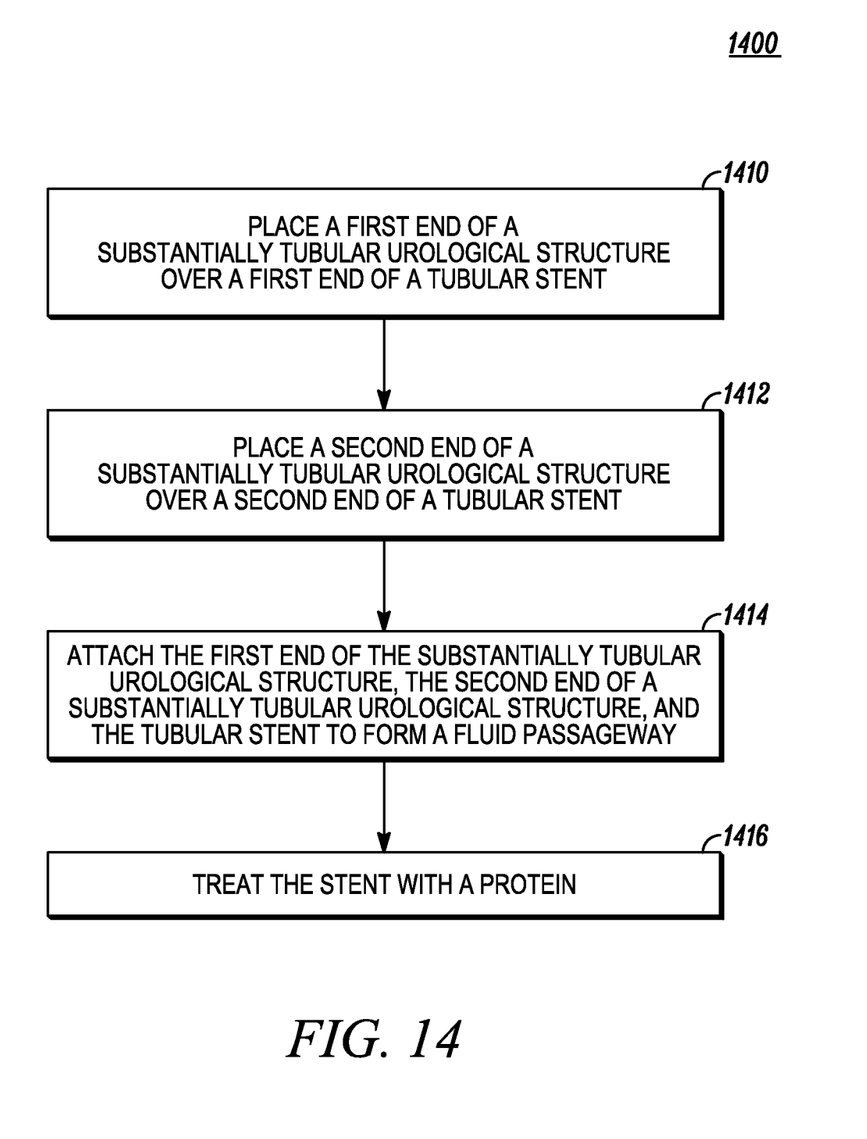
FIG. 14 is a flow chart of yet another method for using a urological repair apparatus, according to an example embodiment.

FIG. 14 is a flow chart of yet another method 1400 for using a urological repair apparatus, according to an example embodiment. The method 1400 of repairing a urological structure includes placing a first end of a substantially tubular urological structure over a first end of a tubular stent 1410, and placing a second end of a substantially tubular urological structure over a second end of a stent 1412, and attaching the first end of the substantially tubular urological structure, the second end of a substantially tubular urological structure, and the tubular stent to form a fluid passageway 1414. In one embodiment, the first end of a substantially tubular urological structure is attached to the first end of a tubular stent, and the second end of the substantially tubular urological structure is attached to the second end of the tubular stent. The method also includes treating the stent with a protein 1416. Also disclosed is a product for repairing the urological structure that uses the methods described above.

Medical technology now allows use of stem cells to grow new bladders. There is evidence that other urological structures may be grown from stem cells or by using other technologies in the future. As a result, an additional procedure that is contemplated includes placing a stent or urological repair apparatus within a baby or child so that they are more likely to be able to receive donor organs or grown organs. For example, in some young children or young babies, the testicles may have to be removed. The seminal vesicle is generally cut and cauterized. When the child grows up, he is no longer capable of having a baby. The procedure would be to place one end of a urological repair apparatus into the seminal vesicle. This would keep the cut end in sufficient shape so that it could be used and reattached many years later when a new organ could be grown or a donor organ would be available.

The foregoing description of the specific embodiments reveals the general nature of the invention sufficiently that others can, by applying current knowledge, readily modify and/or adapt for various applications without departing from the concept, and therefore such adaptations and modifications are intended to be comprehended within the meaning and range of equivalents of the disclosed embodiments.

It is to be understood that the phraseology or terminology employed herein is for the purpose of description and not of limitation. Accordingly, the invention is intended to embrace all such alternatives, modifications, equivalents and variations as fall within the spirit and broad scope of the appended claims.

What we claim:

1. A urological repair device comprising:
    a stent having a substantially continuous outside surface having an uninterrupted radial cross section with a diameter that is adapted to fit within a portion of a urological structure, the stent having a length configured to bridge a distance between a first end of the urological structure and a second end of the urological structure, the stent configured to serve as a backing material as the first end of the urological structure and the second end of the urological structure are stitched together with a sterile needle;
    at least one tapered end, the tapered end enabling placement of the stent within the urological structure; and
    a feature on the exterior surface of the stent for facilitating the attachment of stent to the urological structure, the feature including a plurality of rounded annular barbs having a fixed outer diameter configured to be larger than the inner diameter of the urological structure to provide a friction fit.

2. The urological repair device of claim 1 wherein the stent includes:

a main body;

a first tapered end, and a second tapered end, at least one of the first tapered end and the second tapered end having an inner diameter smaller than the inner diameter of the main body.

3. The urological repair device of claim 1 wherein the stent has an outside diameter configured to fit within a portion of a human ureter and wherein the stent includes:

a main body;

a first tapered end, and a second tapered end, at least one of the first tapered end and the second tapered end having an inner diameter smaller than the inner diameter of the main body, the first tapered end and the second tapered end including the plurality of rounded annular barbs to hold a first portion of a ureter to the first tapered end of the stent and a second portion of the ureter to the second tapered end of the stent.

4. The urological repair device of claim 1 wherein the tapered end enabling placement of the stent within the urological structure includes the plurality of rounded annular barbs.

5. The urological repair device of claim 1 wherein the stent has an outside diameter configured to fit within a portion of a human vas deferens and wherein the stent includes a first tapered end, and a second tapered end, the angle of the taper enabling the placement of at least a portion of the stent into the vas deferens.

6. The urological repair device of claim 1 wherein the stent is made of a biocompatible material.

7. The urological repair device of claim 1 wherein the stent is made of a bioresorbable material.

8. The urological repair device of claim 1 further comprising a liquid protein material to add to the surface of the stent.

9. The urological repair device of claim 8 further comprising:

a length of suture material; and a sterile needle.

10. A urological repair device comprising:

a stent having a substantially continuous outside surface having an uninterrupted radial cross section with a diameter that is adapted to fit within a portion of a urological structure, the stent having a length configured to bridge a distance between a first end of the urological structure and a second end of the urological structure, the configured to serve as a backing material as the first end of the urological structure and the second end of the urological structure are stitched together with a sterile needle;

a first tapered end;

a second tapered end, the first tapered end and the second tapered end enabling placement of the stent within the urological structure; and a first feature on the exterior surface of the stent for facilitating the attachment of stent to the urological structure; and a second feature on the exterior surface of the stent for facilitating the attachment of stent to the urological structure, the first feature and the second feature including a plurality of rounded annular barbs, the plurality of rounded annular barbs having a fixed outer diameter configured to be larger than the inner diameter of the urological structure to provide a friction fit.

11. The urological repair device of claim 10 wherein the plurality of rounded annular barbs of the first feature is configured to hold a first portion of a ureter to the first tapered end of the stent, and wherein the plurality of rounded annular barbs of the second feature is configured to hold a second portion of a ureter to the second tapered end of the stent.

12. The urological repair device of claim 10 wherein the first tapered end includes the plurality of rounded annular barbs of the first feature, and wherein the second tapered end includes the plurality of rounded annular barbs of the second feature.

13. The urological repair device of claim 10 wherein the plurality of rounded annular barbs of the first feature is configured to hold a first portion of a vas deferens to the first tapered end of the stent, and wherein the plurality of rounded annular barbs of the second feature is configured to hold a second portion of a vas deferens to the second tapered end of the stent.

14. The urological repair device of claim 10 further comprising a liquid protein material to add to the surface of the stent.

15. The urological repair device of claim 14 further comprising:

a length of suture material; and a sterile needle.

16. The urological repair device of claim 12 wherein the outer diameter of the rounded barb plurality of rounded barbs near the main body of the stent is larger than the outer diameter of the rounded barb plurality of rounded barbs near the first end or the second end of the stent.

17. A urological repair device comprising:

a stent having a substantially continuous outside surface having an uninterrupted radial cross section with a diameter that is adapted to fit within a portion of a urological structure, the stent having a length configured to bridge a distance between a first end of the urological structure and a second end of the urological structure, the configured to serve as a backing material as the first end of the urological structure and the second end of the urological structure are stitched together with a sterile needle;

a first tapered end;

a second tapered end, the first tapered end and the second tapered end enabling placement of the stent within the urological structure; and a first feature on the exterior surface of the first tapered end of the stent for facilitating the attachment of stent to the urological structure; and a second feature on the exterior surface of the second tapered end of the stent for facilitating the attachment of stent to the urological structure, the first feature and the second feature including a plurality of stacked, rounded annular barbs, at least one of the plurality of stacked, rounded annular barbs having a fixed outer diameter configured to be larger than the inner diameter of the urological structure to provide a friction fit.

* * * * *